& Dellett

United States Patent [19]
Neufeld

[11] 4,409,973
[45] Oct. 18, 1983

[54] METHOD AND APPARATUS FOR CORRECTIVE OSTEOTOMY

[76] Inventor: John A. Neufeld, 20840 Charriere Rd., Oregon City, Oreg. 97045

[21] Appl. No.: 229,641

[22] Filed: Jan. 29, 1981

[51] Int. Cl.³ .................. A61F 5/04; A61F 17/32; A61B 17/16; A61B 17/14
[52] U.S. Cl. .................. 128/92 E; 128/305.1; 128/310; 128/92 EB; 128/317
[58] Field of Search ........... 128/92 R, 92 A, 92 E, 128/92 EB, 305.1, 310, 317; 30/166 R, 144, 355; 83/782, 597; 408/204

[56] References Cited

U.S. PATENT DOCUMENTS

| | | | |
|---|---|---|---|
| D. 245,918 | 9/1977 | Shen | D24/02 |
| 493,730 | 3/1893 | MacKenzie | 128/310 |
| 847,133 | 3/1907 | Velasco | 128/310 |
| 1,231,551 | 7/1917 | Alexander | 408/204 |
| 1,448,697 | 3/1923 | Misener | . |
| 1,669,273 | 5/1928 | Wojnowski et al. | . |
| 2,369,925 | 2/1945 | Smith | 128/317 |
| 2,401,548 | 6/1946 | Chapman | 128/310 |
| 2,557,364 | 6/1951 | Treace | 128/317 |
| 2,737,724 | 3/1956 | Herz | 33/174 |
| 3,554,197 | 1/1971 | Dobble | 128/317 |
| 3,905,374 | 9/1975 | Winter | 128/317 |
| 3,952,412 | 4/1976 | Rhodes | 30/166 R |
| 3,973,862 | 8/1976 | Segal | 408/204 |
| 4,004,581 | 1/1977 | Heimke et al. | 128/305 |
| 4,069,824 | 1/1978 | Weinstock | 128/317 |
| 4,096,964 | 6/1978 | Glick | 408/204 |
| 4,273,117 | 6/1981 | Neuhäuser | 128/310 |
| 4,284,080 | 8/1981 | Rehder | 128/317 |
| 4,312,079 | 1/1982 | Dörre et al. | 128/92 E |

FOREIGN PATENT DOCUMENTS 477722  8/1975  U.S.S.R. .................. 128/92 E

OTHER PUBLICATIONS

Orthopedic Equipment Co., Inc., Burbon, Ind., "Ossotome ® Pneumatic Surgical System", Section of Catalog, 1976.

*Primary Examiner*—C. Fred Rosenbaum
*Assistant Examiner*—C. W. Shedd
*Attorney, Agent, or Firm*—Klarquist, Sparkman, Campbell, Leigh, Whinston & Dellett

[57] ABSTRACT

In high tibial osteotomy a cross-shaped gauge having downwardly-depending side arms is positioned toward the end of the tibia, with the depending arms adjacent the arcuate path of the proposed saw cut. The cross-shaped gauge establishes a first indicia between said depending arms for positioning the arcuate axis of a semi-cylindrical saw, and a second indicia proximate the upper end of the longitudinal arm of the gauge for locating the saw arc. A saw blade of correct radius is then selected. The first indicia established by the gauge positions a first hole drilled through the bone for receiving a guide pin or rod, and the second indicia locates a second hole on the saw line for receiving a depth gauge. An arm on the depth gauge is aligned with a plurality of spacers placed on the aforementioned pin or rod, and the pin or rod is received along a cylindrical bore in the saw. When the saw is operated, the spacers arrest movement of the saw blade when it has passed through the bone.

3 Claims, 9 Drawing Figures

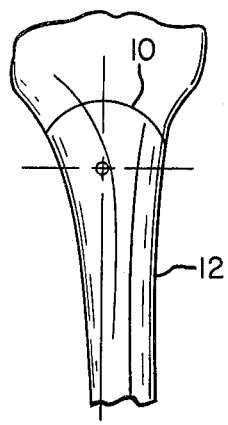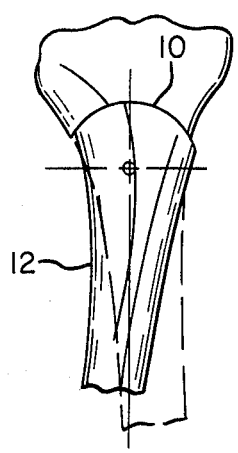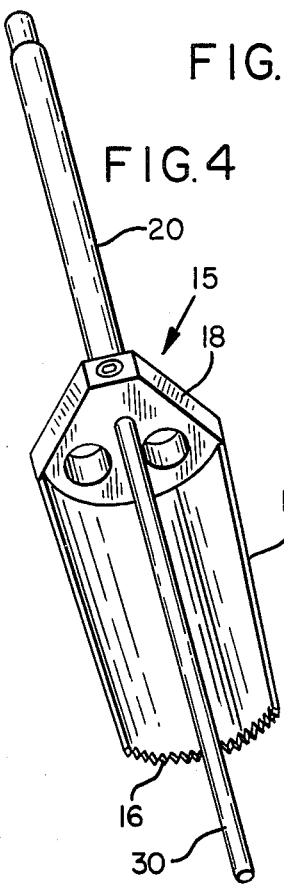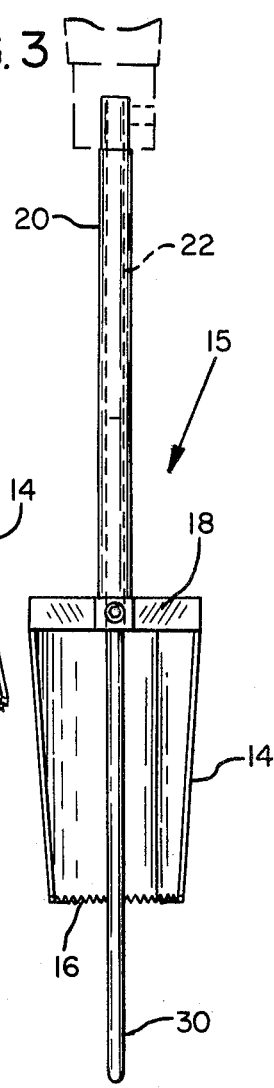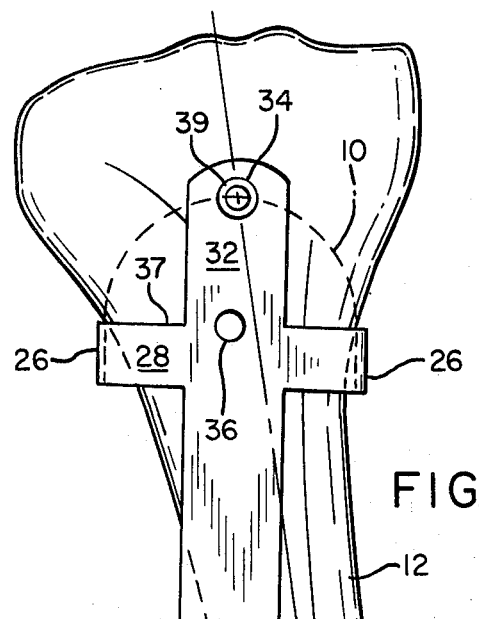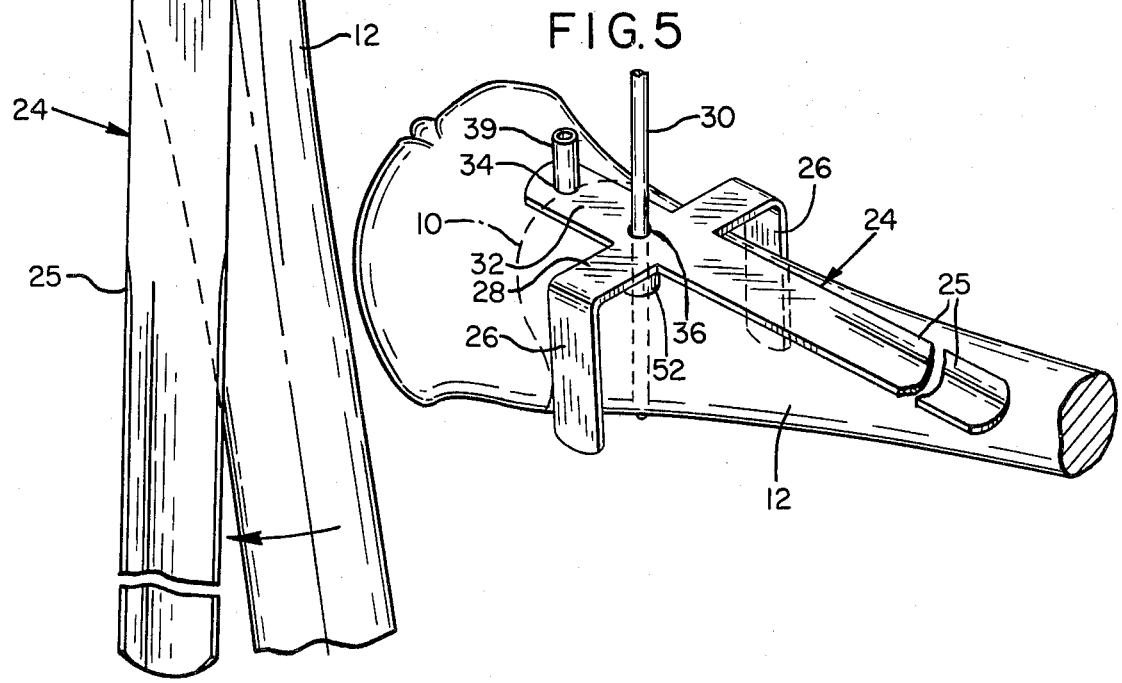

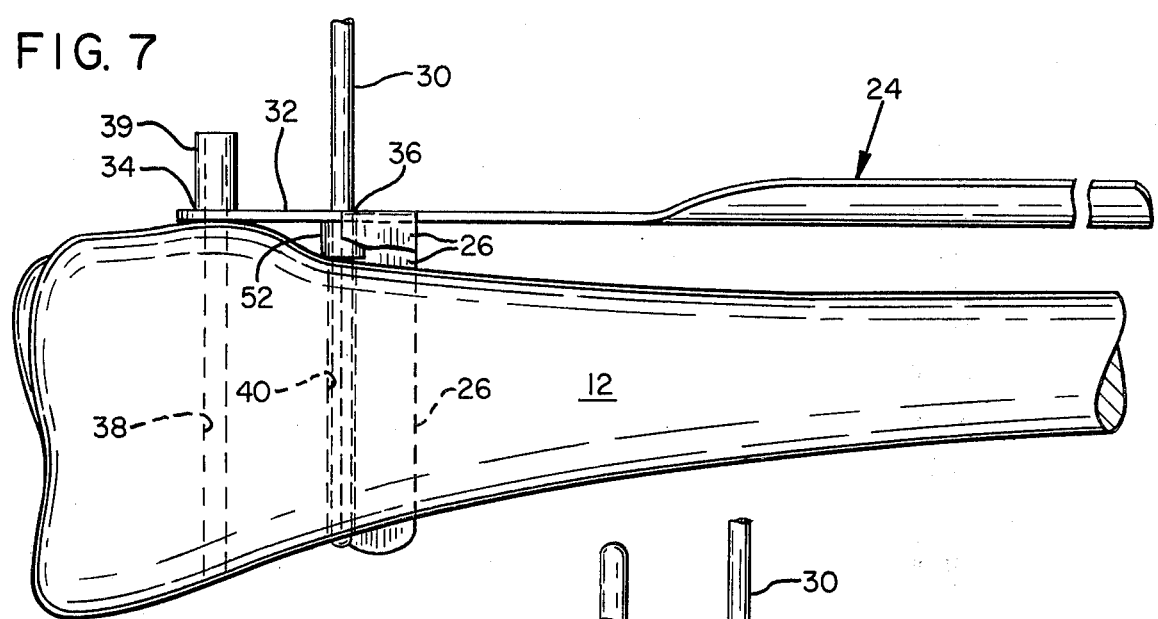
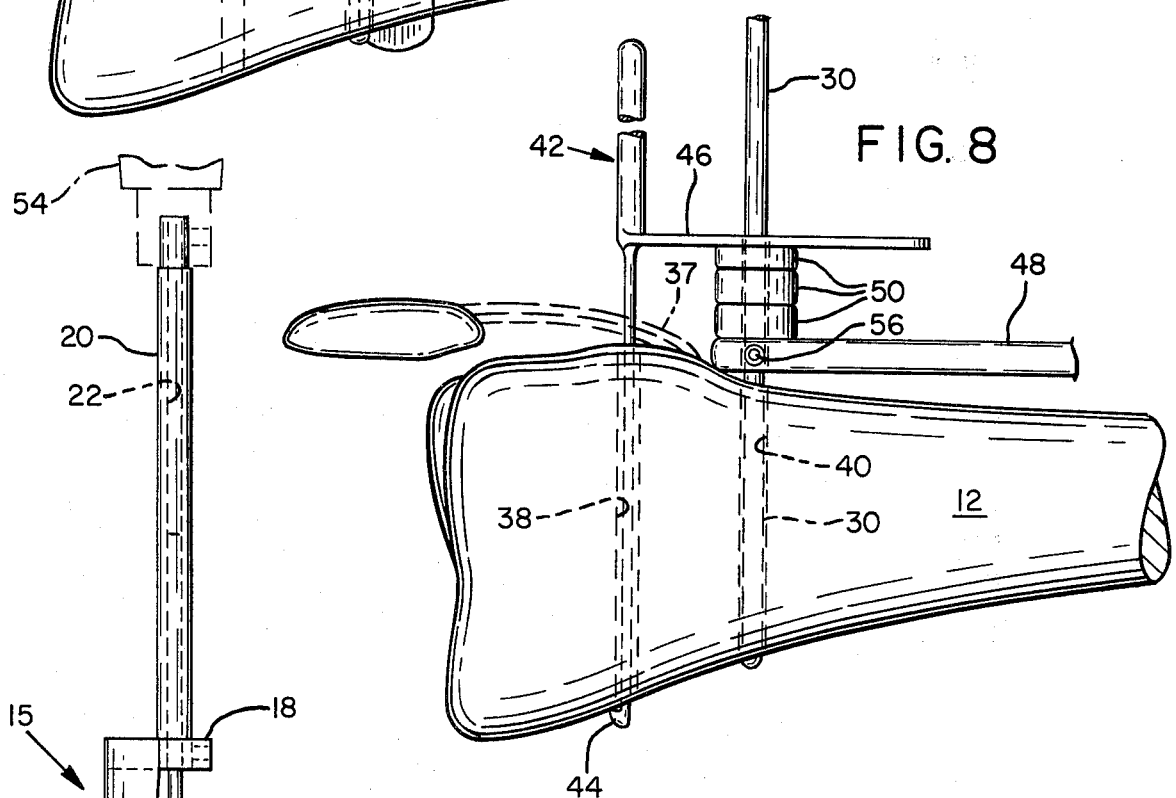
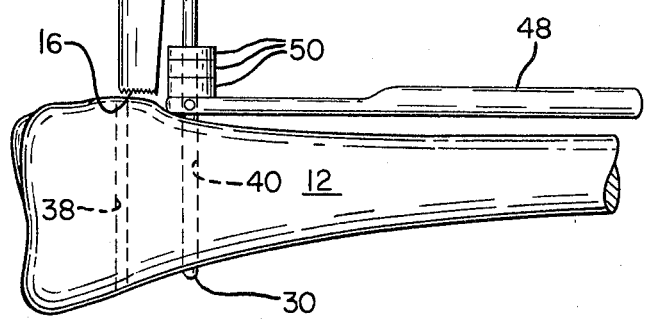

METHOD AND APPARATUS FOR CORRECTIVE OSTEOTOMY

BACKGROUND OF THE INVENTION

The present invention relates to corrective osteotomy and apparatus for performing the same, and particularly to a method and apparatus for performing an arcuate osteotomy with greater accuracy and with less chance of damage to surrounding tissue.

An arcuate osteotomy is a surgical procedure for severing a bone with a semi-cylindrical saw in such manner that a portion of the bone can be reoriented in direction by pivoting the same with respect to the axis of the cut. In particular, the direction of a tibia can be altered in this manner to straighten the leg of a patient.

Procedures of this type may be performed essentially by sight after a skilled surgeon assesses or measures for the desired correction as well as the size and position of the saw to be employed. The correct positioning of the saw may depend upon the skill of the surgeon, but at best is liable to be non-uniform. Moreover, a slight movement of the saw farther than intended, or in a direction not intended, can cause unnecessary damage to surrounding tissue.

SUMMARY OF THE INVENTION

In accordance with the present invention, in a particular embodiment thereof, a corrective osteotomy involves selecting a gauge with depending arms for disposition immediately on either side of a bone on which the osteotomy is to be performed with said arms being spaced apart to lie adjacent the path of the desired cut. The bone is then sawn through with a semi-cylindrical saw selected to provide the correct arc, preferably having an arc diameter equaling the spacing between the depending arms, and having its center aligned between the arms.

In particular, a gauge is employed having central indicia between said depending arms in the form of a hole or tubular member through which a drill bit is aligned for drilling through the bone. A pin or rod is then inserted through such hole. The semi-cylindrical saw is provided with an axial guide bore coincident with the center of its cylindrical cut for slidably receiving the aforementioned pin or rod during sawing. In this manner, the center of cutting is accurately established.

In accordance with another aspect of the present invention, the aforementioned gauge preferably provides indication of the location of the cutting arc in the central region of the bone, and desirably includes indicia for locating a hole through which a depth gauge is inserted having a hooking relation with the underside of the bone. This depth gauge is used in positioning spacers placed on the first mentioned pin or rod for arresting downward motion of the saw.

It is accordingly an object of the present invention to provide an improved method and apparatus for performing a corrective osteotomy.

Another object of the present invention is to provide an improved method and apparatus for performing a corrective osteotomy with more uniform accuracy and less possibility of error in movement.

It is a further object of the present invention to provide an improved method and apparatus for performing a corrective osteotomy which method and apparatus is less likely to cause unnecessary damage to surrounding tissue.

The subject matter which I regard as my invention is particularly pointed out and distinctly claimed in the concluding portion of this specification. The invention, however, both as to organization and method of operation, together with further advantages and objects thereof, may best be understood by reference to the following drawings wherein like reference characters refer to like elements.

DRAWINGS

FIG. 1 is a forward view of a human tibia illustrating a saw cut for performing a corrective osteotomy;

FIG. 2 illustrates the aforesaid tibia after the corrective procedure;

FIG. 3 is a front view of a semi-cylindrical saw utilized in the osteotomy procedure;

FIG. 4 is a perspective view of the FIG. 3 saw;

FIG. 5 is a perspective view illustrating an initial part of the osteotomy procedure according to the present invention wherein a gauge is employed for locating reference points;

FIG. 6 is a top view of the same bone and gauge as FIG. 5;

FIG. 7 is a side view of the bone and gauge;

FIG. 8 is a further side view of the bone hereinbefore indicated at a further point in the procedure; and FIG. 9 is a side view of the same bone having the saw of FIGS. 3 and 4 located in position for making the desired cut.

DETAILED DESCRIPTION

Referring to the drawings, FIGS. 1 and 2 illustrate, in simplified form, an arcuate osteotomy procedure and in particular a high tibial osteotomy. A saw cut 10 is made high on tibia 12 from the forward side thereof employing a semi-cylindrical, oscillating saw blade of a generally known type. As illustrated in FIG. 2, the lower portion of the tibia is then reoriented, e.g., in a direction for straightening the leg of the patient, with the tibia being turned about the saw cut as a bearing joint. The bone is allowed to heal in the new configuration.

FIGS. 3 and 4 illustrate a semi-cylindrical saw 15 according to the present invention as employed for providing the cut 10. The saw includes a semi-cylindrical and somewhat tapered blade 14 having saw teeth 16 at its forward end, with the blade proceeding rearwardly toward a central end support hub or web portion 18 joined to a shank 20, the latter defining the axis of rotation or rather oscillation of the blade. According to the present invention, the web 18 and shank 20 are provided with a central tubular opening or guide bore 22 extending axially of the web and shank and having an axial centerline defining the axis of rotation of the saw. This opening or bore is employed matingly to receive a guide pin or rod 30 preferably used during the osteotomy procedure as hereinafter more fully described. The pin or rod 30 is substantially smaller in diameter than the arc of blade 14.

Referring to FIGS. 5–7, a gauge 24 is employed according to the present invention for determination of the saw radius and position, and thus to select the proper saw. Said gauge is formed of flat metal and is suitably cross-shaped having a longitudinal arm 25 adapted for extending in a direction generally longitudinal of bone 12, and a perpendicular crossbar 28 having a length equal to the width of the desired cut. At the ends of the crossbar the same is provided with the arms 26 which extend downwardly, as viewed in FIG. 5, the arms being disposed in perpendicular relation to crossbar 28 and longitudinal arm 24. Several gauges 24 will be available to the surgeon and one is selected having depending arms which will extend downwardly immediately adjacent either side of the bone at ends of the desired saw cut. A saw blade is then used which matches the selected gauge. Preferably, the radius of the saw blade is equal to half the length of the crossbar so the actual cut will be substantially semi-circular.

The gauge further includes a hole 36 which may be disposed substantially centrally between side edges of longitudinal arm 24 in line with the upper edge 37 of crossbar 28. Alternatively, hole 36 may be positioned slightly to the left of the centerline of arm 24. In any case hole 36 is adapted to receive guide pin 30 therethrough which will ultimately be received in the central bore 22 of the saw as well as through hole 40 in the bone during the actual sawing operation. A tubular extension 52 (see FIG. 7) is advantageously secured to the underside of arm 24 in perpendicular relation thereto for receiving and guiding pin 30 and the drill bit used for drilling hole 40 in perpendicular relation to the arm 24 and in parallel relation to arms 26. Hole 36 establishes the center axis for the saw cut, and will suitably align with upper edge 37 of the crossbar if the saw cut is to be semi-circular.

Another hole 34 is provided through longitudinal arm 25 along section 32 of the arm located above the crossbar, the center of hole 34 being approximately on the centerline of arm 25 at a distance from the center of hole 36 equal to the radius of the saw cut represented by the particular gauge. A tubular member 39 is advantageously secured to the upper side of arm 25 in coaxial relation to hole 34 so as to align the drill used for drilling hole 38 which will receive a depth gauge described hereinafter. Holes 34 and 36 provide indicia for aligning the arcuate bone cut to be made, i.e., at hole 34 for sighting the arc midway between depending arms 26, and for aligning the center axis of the saw at hole 36.

In use, a given gauge 24 is selected and is urged upwardly on the tibia of the patient with arms 26 disposed on either side of the tibia until arms 26 grasp the sides of the bone and the indicia provided by hole 34 is slightly toward the end of the bone from the patellar tendon 37 (see FIG. 8), i.e., by three to five millimeters. Then, the indicia provided by hole 36 will establish the center axis for the saw blade utilized. The cut should extend proximate the region of the epiphyseal plate.

If the wrong gauge 24 has been selected, e.g., if proper relation to the patellar tendon is not achieved, then a larger or smaller gauge is substituted until the correct determination of the cut can be established. A saw blade is used for the sawing operation which blade corresponds in arcuate radius to the distance between the centers of indicia holes 36 and 34, and which preferably corresponds in arcuate diameter to the length of the crossbar, i.e., with the crossbar length preferably being twice the distance between indicia holes 36 and 34.

As illustrated in FIGS. 5 and 6, the gauge 24 is not urged directly upward in line with the center of bone 12, but is rather angled in the direction of and by the angular amount of the correction desired. Thus, if the tibia is to be angled to the left as was illustrated in FIG. 2, the lower part of arm 25 is angled to the left by the desired amount at the same time the gauge is urged upwardly, and it is determined if the indicia defined by hole 34 places the saw cut at the right location with respect to the patellar tendon. The bearing "cup" thus formed at the distal end of the bone is oriented toward the new direction to be taken by the main part of the tibia as illustrated FIG. 2, whereby there is room for the main portion of the tibia to "tuck under" the bearing joint provided by cut 10 without binding or exerting pressure on a narrow bone segment. It will be noted that as gauge 24 is turned to the left as indicated, the left-hand depending arm 26 in FIG. 6 extends along the arc of cut 10 intersecting the bone perimeter at a greater angle than does the right-hand depending arm 26 and the portion of the arc at the right-hand side of FIG. 6.

It is quite possible, by using holes 36 and 34 or similar indicia on gauge 24, to mark the axial center for a saw 15 and accordingly proceed with the osteotomy. However, it is preferred according to the present invention to drill a hole 40 (FIG. 7) straight through the bone in perpendicular relation to gauge 24 employing a conventional drill bit guided by hole 36 and tubular extension 52, after which guide pin 30 is inserted through the hole 40. The guide pin 30 then establishes the rotating or oscillating center for the saw, with the saw slidably receiving pin 30 into its tubular opening or guide bore 22 as illustrated in FIG. 9. The shank 20 of saw 15 is received in the chuck of an oscillating drive motor 54 as illustrated in FIG. 9, and is urged downwardly for performing the desired cut through the bone.

According to a further aspect of the present invention, damage to tissue on the opposite side of the bone is avoided by employing a depth gauge system before the saw is utilized for the cutting operation. Referring particularly to FIGS. 7 and 8, hole 38 is suitably drilled with a conventional drill bit through the bone employing hole 34 and tubular member 39 as a guide, the hole 38 extending in perpendicular relation to gauge 24 and in parallel relation to hole 40. The hole 38, which will be located at the radius of the proposed saw cut, is drilled through hole 34 with a conventional drill bit while the gauge 24 is still in place. Alternatively, hole 38 is drilled at a location as previously indicated by hole 34 of gauge 24 if the latter has been removed. The location of hole 38 under indicating hole 34 will, of course, be as determined with the gauge 24 angularly positioned as shown in FIG. 6.

With gauge 24 removed, pin 30 is inserted through a hole 40 drilled as previously described. Pin 30 is desirably provided with a right angle handle 48 secured thereto by means of set screw 56 at a point such that the lower part of pin 30 can protrude just through the bone with the handle proximate the top of the bone. The surgeon's assistant will ordinarily hold handle 48. A depth gauge 42 is inserted through the aforementioned hole 38, said depth gauge having a lower hook 34 adapted to extend just under the lower side of the bone, and having a right angle handle or arm 46 spaced above hook 44 by a distance equaling the length of saw blade 14 between teeth 16 and the underside of supporting web 18. With the pin 30 in place, and with depth gauge 42 positioned as illustrated in FIG. 8 having its hook 44 just caught at the lower end of hole 38, arm 46 is extended toward the location of pin 30. Toroidal spacers 50, formed of metal or plastic, are slid over pin 30 above arm 48 up to the level of arm 46. Depth gauge 42 can now be removed and the saw 15 positioned over pin 30 as illustrated in FIG. 9 with pin 30 received into mating bore 22. Inasmuch as the depth gauge 42 has a height to the top of toroidal members 50 equal to the length of blade 14 up to the underside of supporting web 18, then downward sawing action of the saw 15 will be arrested as web 18 encounters the uppermost toroidal member 50. At this time, teeth 16 of the saw blade will have just passed through the bone at the central location of hole 38 without unnecessarily contacting tissue therebelow.

Rather than employing toroidal spacers 50, a single such spacer provided with a set screw may be used for securing such spacer to the rod or pin 30 at the proper level just under arm 46.

As a further alternative to embodiments of the present invention, pin 30 may itself comprise a drill bit or have a lower tip comprising a drill bit whereby removing a drill bit and inserting a separate pin 30 is avoided. After drilling, the gauge 24 is slipped off the drill bit and the same is utilized as described hereinbefore to guide the downward movement of saw 15.

It will be seen that the method and apparatus according to the present invention is more conducive to accurate results than a procedure wherein a cut is made approximately by sight. Not only is a more uniform result achieved, but there is also a likelihood of less damage to surrounding tissue.

While I have shown and described various embodiments of my invention, it will be apparent to those skilled in the art that many changes and modifications may be made without departing from my invention in its broader aspects. I therefore intend the appended claims to cover all such changes and modifications as fall within the true spirit and scope of my invention.

I claim:

1. An arcuate osteotomy saw comprising:
   a semi-cylindrical blade of substantially uniform thickness so as to be semi-cylindrical exteriorly and interiorly, said blade having teeth at a forward end thereof adapted for making an arcuate bearing joint cut through a bone as said blade is oscillated about its longitudinal axis to provide for reorientation of said bone about said bearing joint cut,
   and a central guide rod substantially smaller in diameter than said blade for reception in a guide hole drilled in said bone,
   said saw having a central portion longitudinally remoed from said forward end, wherein said central portion is provided with a central bore for receiving said guide rod in bearing relation for guiding said saw relative to said bone, said guide rod having a length extending from said saw for reception in sliding relation substantially through said bone as well as through a substantial length of said central bore to provide said bearing relation so as to guide the saw in the direction determined by said rod.

2. The osteotomy saw according to claim 1 wherein said central portion comprises an end support for said semi-cylindrical blade and is provided with a shank member extending axially away from said forward end of said blade and adapted to be driven by motive means, said central bore being provided by said shank member.

3. An arcuate osteotomy saw comprising:
   a semi-cylindrical blade of substantially uniform thickness so as to be semi-cylindrical exteriorly and interiorly, said blade having teeth at a forward end thereof adapted for making an arcuate bearing joint cut through a bone as said blade is oscillated about its longitudinal axis to provide for reorientation of said bone about said bearing joint cut,
   and a central guide rod substantially smaller in diameter than said blade for reception in a guide hole drilled in said bone,
   said saw having a central portion longitudinally removed from said forward end, wherein said central portion is provided with means for receiving said guide rod in bearing relation for guiding said saw relative to said bone, said guide rod having a length extending from said saw for slidable reception substantially through said bone as well as in supporting relation to said central portion to provide bearing action for guiding the saw in the direction determined by said rod.

* * * * *